(12) United States Patent
Hansen

(10) Patent No.: US 6,451,974 B1
(45) Date of Patent: Sep. 17, 2002

(54) METHOD OF ACYLATING PEPTIDES AND NOVEL ACYLATING AGENTS

(75) Inventor: Louis Brammer Hansen, Værløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/523,783

(22) Filed: Mar. 13, 2000

Related U.S. Application Data

(60) Provisional application No. 60/126,882, filed on Mar. 30, 1999.

(30) Foreign Application Priority Data

Mar. 17, 1999 (EP) .............................. 99610019

(51) Int. Cl.$^7$ ........................... C07K 1/00; G01N 33/68
(52) U.S. Cl. ..................... 530/345; 530/308; 530/333; 530/402; 436/86; 436/90
(58) Field of Search ................................ 530/345, 308, 530/333, 402; 436/86, 90

(56) References Cited

U.S. PATENT DOCUMENTS

| | | | |
|---|---|---|---|
| 4,497,729 A | | 2/1985 | Kitaura et al. ............. 530/333 |
| 4,619,915 A | | 10/1986 | Ives ............................. 514/17 |
| 5,216,125 A | * | 6/1993 | Kouge ........................ 530/345 |
| 5,468,843 A | * | 11/1995 | Boyd et al. ................. 530/345 |
| 5,512,549 A | * | 4/1996 | Chen et al. .................. 514/12 |

FOREIGN PATENT DOCUMENTS

| | | |
|---|---|---|
| EP | 0511 600 | 11/1992 |
| EP | 0712 862 | 5/1996 |
| WO | WO 91/11457 | 8/1991 |
| WO | WO 98/02460 | 1/1998 |
| WO | WO 98/08871 | 3/1998 |
| WO | WO 98/08872 | 3/1998 |
| WO | WO 99/43708 | 9/1999 |

OTHER PUBLICATIONS

Meguro et al., Chem. Pharm. Bull., vol. 34, No. 7, pp. 2840–2851, 1986.*
Abstract, Miroshnikov et al, ZCAPLUS accession No. 1970:415243.
Meguro et al., Chem. Pharm. Bull., vol. 34, No. 7, (1986).

* cited by examiner

Primary Examiner—Christopher S. F. Low
Assistant Examiner—Abdel A. Mohamed
(74) Attorney, Agent, or Firm—Rezo Green, Esq.; Richard W. Bork, Esq.

(57) ABSTRACT

Provided is a method for acylating one or more amino groups of a peptide or protein such as GLP-1. This method includes (a) reacting a peptide or protein having at least one free amino group with an acylating agent of formula I

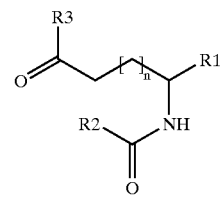

wherein n is 0–8; $R^1$ is $COOR^4$; $R^2$ is a lipophilic moiety; $R^3$ and its attached carboxyl group designate a reactive ester or a reactive N-hydroxy imide ester; and $R^4$ is selected from hydrogen, $C_{1-12}$-alkyl and benzyl, under basic conditions in a mixture of an aprotic polar solvent and water; and (b) if $R^4$ is not hydrogen, saponifying the acylated peptide or protein ester group under basic conditions in order to obtain an N-acylated peptide or an N-acylated protein.

17 Claims, No Drawings

METHOD OF ACYLATING PEPTIDES AND NOVEL ACYLATING AGENTS

CROSS-REFERENCE TO RELATED APPLICATIONS

This application claims priority under 35 U.S.C. 119 of U.S. provisional application No. 60/126,882 filed Mar. 30, 1999 and European Patent Application No. 99610019.4 filed Mar. 17, 1999, the contents of which are fully incorporated herein by reference.

BACKGROUND OF THE INVENTION

1. Field of the Invention

The present invention relates to a method of introducing one or more acyl groups into a peptide or a protein. More particularly, the invention relates to an improved method of acylating the ε-amino group of a lysine residue contained in a naturally occurring GLP-1 or an analogue thereof. Furthermore, the present invention relates to compounds useful as acylating agents in the method.

2. Description of the Related Art

Peptides are widely used in medical practice, and since they can be produced by recombinant DNA technology, it can be expected that their importance will increase also in the years to come. When native peptides or analogues thereof are used in therapy, it is generally found that they have a high clearance. A high clearance of a therapeutic agent is inconvenient in cases where it is desired to maintain a high blood level thereof over a prolonged period of time since repeated administrations will then be necessary. Examples of peptides which in their native form have a high clearance are: ACTH, corticotropin-releasing factor, angiotensin, calcitonin, exendin, exendin-3, exendin4, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease.

Introduction of lipophilic acyl groups into naturally occurring peptides or analogues thereof leads to acylated peptides which have a protracted profile of action relative to the native peptide (or unmodified analogue). This phenomenon has been thoroughly described and demonstrated in the present applicant's previous applications, WO98/08871, which i.a. discloses acylation of GLP-1 and analogues, and WO98/08872, which i.a. discloses acylation of GLP-2 and analogues, and WO99/43708, which i.a. discloses acylation of exendin and analogues. Furthermore, it has been suggested that the inclusion of a group which can be negatively charged, e.g., a carboxylic acid group, adjacent to the lipophilic group may be advantageous.

European patent application No. 92107035.5 (Kuraray Co.) describes reactive monoesters of long chain dicarboxylic acids for the introduction of long chain carboxylic acids into proteins. Introduction of lipophilic acyl groups into GLP-1 via mono- or dipeptide spacers may be especially interesting and has been suggested and exemplified in WO98/08871. Asparatic acid and glutamic acid were mentioned as suitable linkers. However, as such mono- and dipeptide spacers include a supplementary carboxylic acid group, protection and subsequent deprotection steps were considered necessary. Deprotection was performed under acidic conditions which to a certain degree led to destruction of the peptide (GLP-1). Thus, alternative methods for the preparation of these variants are desirable.

Thus, it has been the aim of the present invention to provide an alternative method for the introduction of lipophilic groups into peptides via α-amino-α, ω-dicarboxylic acid spacers. Such a method will facilitate the preparation of modified peptides where chargeable carboxylic acid groups are introduced in the proximity of lipophilic groups, but without direct influence on the lipophilic group.

SUMMARY OF THE INVENTION

The present invention provides a method for acylating one or more amino groups of a peptide (or protein), the method comprising:

(a) reacting a peptide (or protein) having at least one free amino group with an acylating agent of formula I

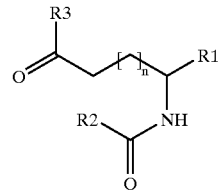

wherein
n is 0–8;
$R^1$ is $COOR^4$;
$R^2$ is a lipophilic moiety, e.g., selected from $C_{3-39}$-alkyl, $C_{3-39}$-alkenyl, $C_{3-39}$-alkadienyl and steroidal residues;
$R^3$ together with the carboxyl group to which $R^3$ is attached designate a reactive ester or a reactive N-hydroxy imide ester; and
$R^4$ is selected from hydrogen, $C_{1-12}$-alkyl and benzyl, under basic conditions in a mixture of an aprotic polar solvent and water; and (b) if $R^4$ is not hydrogen, saponifying the acylated peptide ester group ($COOR^4$) under basic conditions;

in order to obtain an N-acylated peptide (or an N-acylated protein).

It has been found that saponification of the acylated peptide ester (where $R^4$ is an alkyl or benzyl group) under basic conditions is possible with only minor or no racemization of the various α-amino acid fragments of the peptide and the spacer. The present invention has been found to have certain advantages over the previously used acidic hydrolysis with respect to purity and suppression of side products, e.g. degradation products.

It has also been found that acylation using the acylating agent as the free acid (where $R^4$ is hydrogen) under basic conditions does essentially lead directly to the desired product, the acylated peptide, without side products and without the need for a deprotection step.

The present invention also provides novel compounds useful as acylating agents in the above-mentioned method, such novel compounds having formula I

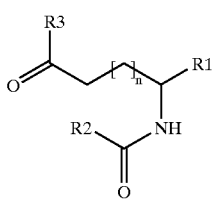

wherein n is 0–8;

$R^1$ is COOH;

$R^2$ is a lipophilic moiety, e.g., selected from $C_{3-39}$-alkyl, $C_{3-39}$-alkenyl, $C_{3-39}$-alkadienyl and steroidal residues; and $R^3$ together with the carboxyl group to which $R^3$ is attached designate a reactive ester or a reactive N-hydroxy imide ester.

DETAILED DESCRIPTION OF THE INVENTION

Peptides and Proteins

It is generally believed that the present invention is useful for the introduction of lipophilic acyl groups into any peptide (or protein) in order to reduce the in vivo clearance rate. Examples of such peptides and proteins are ACTH, corticotropin-releasing factor, angiotensin, calcitonin, exendin and analogues thereof, insulin and analogues thereof, glucagon and analogues thereof, glucagon-like peptide-1 and analogues thereof, glucagon-like peptide-2 and analogues thereof, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease.

It should be understood that the peptide (or protein) should carry at least one free amino group, such an amino group being the N-terminal amino group or a side chain amino group.

Particularly interesting are amino groups of lysine and ornithine amino acid residues. The method is particularly relevant for the N-acylation of the ε-amino group of lysine residues. It should also be understood that the peptide or protein in question may comprise two or more pendant amino groups which all may be N-acylated according to the present invention.

It is presently believed that the present invention is especially suitable for the modification of GLP-1 and analogues thereof. Examples of GLP-1 and analogues which can be N-acylated according to the present invention are GLP-1 and truncated analogues, such as $Arg^{26}$-GLP-1 (7–37); $Arg^{34}$-GLP-1(7–37); $Lys^{36}$-GLP-1(7–37); $Arg^{26,34}Lys^{36}$-GLP-1(7–37); $Arg^{26,34}Lys^{38}$GLP-1(7–38); $Arg^{28,34}Lys^{39}$-GLP-1(7–39); $Arg^{26,34}Lys^{40}$-GLP-1(7–40); $Arg^{26}Lys^{36}$-GLP-1(7–37); $Arg^{34}Lys^{36}$-GLP-1(7–37); $Arg^{26}Lys^{39}$-GLP-1(7–39); $Arg^{34}Lys^{40}$-GLP-1(7–40); $Arg^{26,34}Lys^{36,39}$-GLP-1(7–39); $Arg^{26,34}Lys^{36,40}$-GLP-1 (7–40); $Gly^8Arg^{26}$-GLP-1(7–37); $Gly^8Arg^{34}$-GLP-1(7–37); $Gly^8Lys^{36}$-GLP-1(7–37); $Gly^8Arg^{26,34}Lys^{36}$-GLP-1(7–37); $Gly^8Arg^{26,34}Lys^{39}$-GLP-1(7–39); $Gly^8Arg^{26,34}Lys^{40}$-GLP-1(7–40); $Gly^8Arg^{26}Lys^{36}$-GLP-1(7–37); $Gly^8Arg^{34}Lys^{36}$-GLP-1(7–37); $Gly^8Arg^{26}$-GLP-1(7–39); $Gly^8Arg^{34}Lys^{40}$-GLP-1(7–40); $Gly^8Arg^{26,34}Lys^{36,39}$-GLP-1(7–39); $Gly^8Arg^{36,34}Lys^{36,40}$-GLP-1(7–40); $Arg^{26,34}Lys^{38}$GLP-1 (7–38); $Arg^{26,34}Lys^{39}$GLP-1(7–39); $Arg^{26,34}Lys^{40}$GLP-1 (7–40); $Arg^{26,34}Lys^{41}$GLP-1(7–41); $Arg^{26,34}Lys^{42}$GLP-1 (7–42); $Arg^{26,34}Lys^{43}$GLP-1(7–43); $Arg^{26,34}Lys^{44}$GLP-1 (7–44); $Arg^{26,34}Lys^{45}$GLP-1(7–45); $Arg^{26,34}Lys^{38}$GLP-1 (1–38); $Arg^{26,34}Lys^{39}$GLP-1(1–39); $Arg^{26,34}Lys^{40}$GLP-1 (1–40); $Arg^{26,34}Lys^{41}$GLP-1(1–41); $Arg^{26,34}Lys^{42}$GLP-1 (1–42); $Arg^{26,34}Lys^{43}$GLP-1(1–43); $Arg^{26,34}Lys^{44}$GLP-1 (1–44); $Arg^{26,34}Lys^{45}$GLP-1(1–45); $Arg^{26,34}Lys^{38}$GLP-1 (2–38); $Arg^{26,34}Lys^{39}$GLP-1(2–39); $Arg^{26,34}Lys^{40}$GLP-1 (2–40); $Arg^{26,34}Lys^{41}$GLP-1(2–41); $Arg^{26,34}Lys^{42}$GLP-1 (2–42); $Arg^{26,34}Lys^{43}$GLP-1(2–43); $Arg^{26,34}Lys^{44}$GLP-1 (2–44); $Arg^{26,34}Lys^{45}$GLP-1(2–45); $Arg^{26,34}Lys^{38}$GLP-1 (3–38); $Arg^{26,34}Lys^{39}$GLP-1(3–39); $Arg^{26,34}Lys^{40}$GLP-1 (3–40); $Arg^{26,34}Lys^{41}$GLP-1(3–41); $Arg^{26,34}Lys^{42}$GLP-1 (3–42); $Arg^{26,34}Lys^{43}$GLP-1(3–43); $Arg^{26,34}Lys^{44}$GLP-1 (3–44); $Arg^{26,34}Lys^{45}$GLP-1(3–45); $Arg^{26,34}Lys^{38}$GLP-1 (4–38); $Arg^{26,34}Lys^{39}$GLP-1(4–39); $Arg^{26,34}Lys^{40}$GLP-1 (4–40); $Arg^{26,34}Lys^{41}$GLP-1(4–41); $Arg^{26,34}Lys^{42}$GLP-1 (4–42); $Arg^{26,34}Lys^{43}$GLP-1(4–43); $Arg^{26,34}Lys^{44}$GLP-1 (4–44); $Arg^{26,34}Lys^{45}$GLP-1(4–45); $Arg^{26,34}Lys^{38}$GLP-1 (5–38); $Arg^{26,34}Lys^{39}$GLP-1(5–39); $Arg^{26,34}Lys^{40}$GLP-1 (5–40); $Arg^{26,34}Lys^{41}$GLP-1(5–41); $Arg^{26,34}Lys^{42}$GLP-1 (5–42); $Arg^{26,34}Lys^{43}$GLP-1(5–43); $Arg^{26,34}Lys^{44}$GLP-1 (5–44); $Arg^{26,34}Lys^{45}$GLP-1(5–45); $Arg^{26,34}Lys^{38}$GLP-1 (6–38); $Arg^{26,34}Lys^{39}$GLP-1(6–39); $Arg^{26,34}Lys^{40}$GLP-1 (6–40); $Arg^{26,34}Lys^{41}$GLP-1(6–41); $Arg^{23,34}Lys^{42}$GLP-1 (6–42); $Arg^{26,34}Lys^{43}$GLP-1(6–43); $Arg^{26,34}Lys^{44}$GLP-1 (6–44); $Arg^{26,34}Lys^{45}$GLP-1(6–45); $Arg^{26}Lys^{38}$GLP-1 (1–38); $Arg^{34}Lys^{38}$GLP-1(1–38); $Arg^{26,34}Lys^{36,38}$GLP-1 (1–38); $Arg^{26}Lys^{38}$GLP-1(7–38); $Arg^{34}Lys^{38}$GLP-1(7–38); $Arg^{26,34}Lys^{36,38}$GLP-1(7–38); $Arg^{26,34}Lys^{38}$GLP-1(7–38); $Arg^{26}Lys^{39}$GLP-1(1–39); $Arg^{34}Lys^{39}$GLP-1(1–39); $Arg^{26,34}Lys^{36,39}$GLP-1(1–39); $Arg^{26}Lys^{39}$GLP-1(7–39); $Arg^{34}Lys^{39}$GLP-1(7–39); $Arg^{26,34}Lys^{36,39}$GLP-1(7–39); $Arg^{26}$GLP-1(7–37), $Arg^{34}$-GLP-1(7–37), $Lys^{36}$-GLP-1 (7–37), $Arg^{26,34}Lys^{36}$-GLP-1(7–37); $Arg^{26}Lys^{36}$-GLP-1 (7–37), $Arg^{34}Lys^{36}$-GLP-1(7–37), $Gly^8Arg^{26}$-GLP-1(7–37), $Gly^8Arg^{34}$-GLP-1(7–37), $Gly^8Lys^{36}$-GLP-1(7–37), $Gly^8Arg^{26,34}Lys^{36}$-GLP-1(7–37), $Gly^8Arg^{26}Lys^{36}$-GLP-1 (7–37); $Gly^8Arg^{34}Lys^{36}$-GLP-1(7–37); $Arg^{26}Lys^{38}$-GLP-1 (7–38), $Arg^{26,34}Lys^{38}$-GLP-1(7–38), $Arg^{26,34}Lys^{36,38}$-GLP-1(7–38), $Gly^8Arg^{26}Lys^{38}$-GLP-1(7–38); $Gly^8Arg^{26,34}Lys^{36,38}$-GLP-1(7–38); $Gly^8,Arg^{26,34},Glu^{37},Lys^{38}$-GLP-1 (7–38), $Arg^{26}Lys^{39}$-GLP-1(7–39), $Arg^{26,34}Lys^{36,39}$-GLP-1 (7–39), $Gly^8Arg^{26}Lys^{39}$-GLP-1(7–39); $Gly^8Arg^{26,34}Lys36, 39$-GLP-1(7–39); $Arg^{34}Lys^{40}$-GLP-1(7–40), $Arg^{26,34}Lys^{36,40}$-GLP-1(7–40), $Gly^8Arg^{34}Lys^{40}$-GLP-1(7–40) and $Gly^8Arg^{26,34}Lys^{36,40}$-GLP-1(7–40). Each of these GLP-1 analogues and truncated analogues constitutes alternative embodiments of the present invention.

It is presently believed that the present invention is also especially suitable for the modification of GLP-2 and analogues thereof. Examples of GLP-2 and analogues which can be N-acylated according to the present invention are GLP-2 analogues and truncated analogues, such as $Lys^{20}GLP-2(1-33)$; $Lys^{20}Arg^{30}GLP-2(1-33)$; $Arg^{30}Lys^{34}GLP-2(1-34)$; $Arg^{30}Lys^{35}GLP-2(1-35)$; $Arg^{30,35}Lys^{20}GLP-2(1-35)$; and $Arg^{35}GLP-2-(2-35)$; Each of these GLP-2 analogues and truncated analogues constitutes alternative embodiments of the present invention.

It is presently believed that the present invention is also especially suitable for the modification of exendin and analogues thereof. Examples of exendin and analogues which can be N-acylated according to the present invention are exendin analogues and truncated analogues, such as exendin-3 and exendin-4. Each of these exendin analogues and truncated analogues constitutes alternative embodiments of the present invention.

In a further embodiment of the present invention the N-acylation takes place at the ε-amino group of lysine residues.

The effects of GLP-1 and its analogues are thoroughly described in WO098/08871. The effects of GLP-2 and its analogues are thoroughly described in WO098/08872. The effects of exendin and its analogues are thoroughly described in WO99/43708.

Acylating Agent

In the method according to the invention, a peptide (or protein) which has at least one free amino group is reacted with an acylating agent of formula I

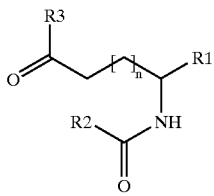

The integer n in formula I is preferably 0–8, in particular 0–6 corresponding, e.g., to aspartic acid, glutamic acid, etc. Preferably, n is 0–4 such as 0–2, e.g., 0 (aspartic acid) or 1 (glutamic acid). Each of these integers and ranges constitutes alternative embodiments of the present invention.

$R^1$ in formula I represents a free acid group (COOH) or an ester group (COOR$^4$). In the cases where $R^1$ is an ester group, $R^4$ is selected from groups which can be removed (as the corresponding alcohols) by hydrolysis under basic conditions. Examples of such groups are $C_{1-12}$-alkyl, e.g. methyl, ethyl, prop-1-yl, prop-2-yl, but-1-yl, but-2-yl, 2-methyl-prop-1-yl, 2-methyl-prop-2-yl (tert-butyl), hex-1-yl, etc., and benzyl. Each of these groups constitutes alternative embodiments of the present invention.

$R^2$ in formula I represents the lipophilic moiety to be incorporated into the peptide or protein. Such a lipophilic moiety is typically selected from $C_{3-39}$-alkyl, $C_{3-39}$-alkenyl, $C_{3-39}$-alkadienyl and steroidal residues. Specific examples of $C_{3-39}$-alkyl are heptyl, nonyl, undecanyl, tridecanyl, pentadecanyl, heptadecanyl, and nonadecanyl. Each of these lipophilic moieties constitutes alternative embodiments of the present invention.

The lipophilic substituent or moiety is characterized by having a solubility in water at 20° C. in the range from about 0.1 mg/100 ml water to about 250 mg/100 ml water, preferably in the range from about 0.3 mg/100 ml water to about 75 mg/100 ml water. For instance, octanoic acid (C8) has a solubility in water at 20° C. of 68 mg/1 00 ml, decanoic acid (C10) has a solubility in water at 20° C. of 15 mg/100 ml, and octadecanoic acid (C18) has a solubility in water at 20° C. of 0.3 mg/100 ml. Each of these lipophilic substituent ranges constitutes alternative embodiments of the present invention.

The terms "$C_{3-39}$-alkyl", "$C_{3-39}$-alkenyl" and "$C_{3-39}$-alkadienyl" are intended to cover straight chain and branched, preferably straight chain, saturated, mono-unsaturated and di-unsaturated, respectively, hydrocarbon radicals of 3–39 carbon atoms. Specific examples of $C_{3-39}$-alkyl are heptyl, nonyl, undecanyl, tridecanyl, pentadecanyl, heptadecanyl, and nonadecanyl.

When used herein, the term "steroidal residue" is intended to mean a lipophilic group which together with the carbonyl group to which $R^2$ is attached is derived from a steroid carboxylic acid, i.e., a tri-, tetra- and pentacyclic, full saturated or partially unsaturated $C_{16-36}$-hydrocarbon. Examples of such groups $R^2$—C(=O)— are lithocholoyl, deoxycholoyl, and choloyl.

Among the lipophilic groups mentioned above, $C_{7-25}$-alkyl, $C_{7-25}$-alkenyl, $C_{7-25}$-alkadienyl and steroidal residues are especially relevant. Particularly interesting examples are heptyl, nonyl, undecanyl, tridecanyl, pentadecanyl, heptadecanyl, nonadecanyl, lithocholoyl, deoxcholoyl, and choloyl. Each of these lipophilic groups constitutes alternative embodiments of the present invention.

$R^3$ in formula I together with the carboxyl group to which $R^3$ is attached designate a reactive ester or a reactive N-hydroxy imide ester. Each of these esters constitutes alternative embodiments of the present invention. Reactive esters and reactive N-hydroxy imide esters are well known in the art of organic chemistry (especially in peptide chemistry) as functional groups which are used in acylation of amino, thio and hydroxy groups. Within the context of the present invention, the term "reactive ester or a reactive N-hydroxy imide ester" is intended to mean an ester functionalized form of a carboxylic acid group suitable for acylating an amine, preferably a primary amine. It should thus be understood, that selectivity for acylation of primary amines is preferred over acylating of hydroxy and thio groups. Reactive N-hydroxy imide esters are especially preferred.

Examples of reactive esters are 1-hydroxybenzotriazole esters and derivatives. A number of highly effective reagents, e.g., 2-(1H-benzotriazol-1yl)-1,1,3,3,-tetramethyluronium tetrafluoroborate, for the formation of such activated esters of carboxylic acids are known.

Such reactive esters are typically formed in situ in the presence of a base, e.g., an organic base such as a trialkylamine.

Examples of the imide part of reactive N-hydroxy imide esters are those specifically described in European patent application No. 92107035.5, page 13, line 3, to page 17, line 10 (which are hereby incorporated by reference). Especially interesting examples of imide parts among those are succinimide, phthalimide, etc. Each of these imide parts constitutes alternative embodiments of the present invention.

The reactive N-hydroxy imide esters of the formula I can be prepared by condensation of the corresponding acid (i.e. the N-acylated α-carboxy protected diacid ($R^4$ is not hydrogen)) with an equimolar amount (e.g. 0.95–1.05 mole, preferably 1.0 mole) of the N-hydroxy-imide of the corresponding imide. (The N-acylated α-carboxy protected diacid is on the other hand typically prepared from the corresponding α-carboxy protected, α-aminodiacid and a benzotriazole ester of the lipophilic moiety. This benzotriazole ester can, e.g., be prepared from the acid chloride and the benzotriazole or from the free acid and the benzotriazole by DCC coupling as described in WO 98/02460 (Examples 1–3).) The condensation is typically performed under dehydration conditions, e.g., in the presence of a coupling reagent such as a carbodiimide coupling reagent (e.g. dicyclohexylcarbodiimide (DCC)). The coupling reagent, when present, is preferably added in equimolar amounts relative to the acid. The reaction is typically performed in a polar aprotic solvent such as anhydrous tetrahydrofuran (THF), anhydrous dimethylformamide (DMF), anhydrous acetone, anhydrous dichloromethane, anhydrous dioxane, anhydrous dimethylacetamide, or anhydrous N-methyl-2-pyrrolidone (NMP). The reaction is typically performed at a temperature in the range of 0–50° C., e.g., 5–30° C. such as room temperature, for a period of 1–96 hours, such as 4–36 hours. One possible set of reagents and conditions is as follows. The N-hydroxy-imide (e.g. succinimide or phthalimide) and the acid in question in an approximately 1:1 molar ratio are dissolved in anhydrous THF or anhydrous DMF (or a mixture thereof) and an equimolar amount of DCC is added to the solution. After completion of the reaction between the N-hydroxy-imide and the acid, the product is isolated and purified using conventional means such as filtration (filtration of precipitated dicyclohexylurea (DCU) when DCC is used as coupling reagent), crystallization, recrystallization, chromatography, etc. One possible purification route includes removal of precipitated used coupling reagent by filtration, evaporation of the solvent under reduced pressure, resuspension of the product, e.g., in acetone, filtration, crystallization by addition of a non-polar solvent, e.g., hexane, and optionally recrystallization and/or washing. The product may be used directly as the acylating reagent of the formula I in the method according to the invention.

In the event where the acylating reagent of the formula I is to be used as the free α-carboxylic acid ($R^4$=hydrogen), a compound of the formula I where $R^4$ is a group which can be removed selectively is converted to the corresponding compound where $R^4$ is hydrogen. The carboxylic acid protecting group may be a benzyl group which can be removed by catalytic hydrogenation or an allyl group which can be selectively removed. A benzyl protecting group may be removed by catalytic hydrogenation in an aprotic polar solvent, e.g., in acetone, at room temperature by using palladium-on-carbon and hydrogen. The reaction may be performed in a closed vessel with a hydrogen atmosphere (typically 0.1–10 atm) under vigorous stirring. The reaction is typically completed within 0.5–12 hours depending on the quality of the palladium catalyst. Conventional work-up applies.

It is believed that the compounds of the formula I where $R^4$ is hydrogen are novel as such and, thus, those compounds constitute a special aspect of the present invention. Thus, the present invention also provides novel compounds of formula I

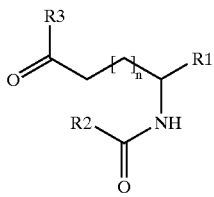

wherein
  n is 0–8;
  $R^1$ is COOH;
  $R^2$ is a lipophilic moiety, preferably selected from $C_{3-39}$-alkyl, $C_{3-39}$-alkenyl, $C_{3-39}$-alkadienyl and steroidal residues; and
  $R^3$ together with the carboxyl group to which $R^3$ is attached designate a reactive ester or a reactive N-hydroxy imide ester.

Reaction Conditions

The reaction between the acylating agent of the formula I and the peptide or protein is performed under basic conditions in a mixture of an aprotic polar solvent and water.

The acylating agent of the formula I is typically used in a slight excess relative to the number of amino groups of the peptide to be acylated. The ratio is typically 1:1 to 1:20 with an excess of the acylating agent, preferably 1:1.2 to 1:5, taking into account the number of amino groups in the peptide.

It should be understood that the peptide may be fully N-acylated or only partially N-acylated depending on the amount of acylating agent used and the reaction conditions. It is preferred that the N-acylation is substantially stochiometrical.

Typically, the aprotic polar solvent is selected from anhydrous tetrahydrofuran (THF), anhydrous dimethylformamide (DMF), acetone, dichloromethane, dimethylsulfoxide (DMSO), dioxane, dimethylacetamide, and N-methyl-2-pyrrolidone and mixtures thereof, among which dimethylformamide, dimethylsulfoxide, dimethylacetamide and N-methyl-2-pyrrolidone are preferred and N-methyl-2-pyrrolidone is especially preferred. The ratio between the aprotic polar solvent and water (e.g. N-methyl-2-pyrrolidone and water) is typically 1:10 to 10:1, in particular 1:5 to 5:1, especially 1:1 to 3:1.

The temperature is typically kept in the range of –10–50° C., preferably in the range of 0–25° C.

It is important that the pH value of the solvent mixture is in the range of 7–14, such as 9–13, preferably in the range of 9.5–12.5, in order for the reaction to proceed smoothly. The result with respect to yield and purity is normally optimal when the pH value of the solvent mixture is in the range of 10–12. The desired pH value is obtained by addition of alkalimetal hydroxides, e.g., sodium hydroxide and potassium hydroxide, and/or organic bases such as trialkylamines (e.g. triethylamine, N,N-diisopropylethylamine, etc.)

As a typical example, the reaction in step (a) is performed using the protein and the acylating agent of the formula I in a 1:1 to 1:5 molar ratio. The peptide is typically pre-dissolved in water at –10–30° C. such as 0–25° C. and the pH is adjusted to the desired level using an alkalimetal hydroxide (e.g. sodium hydroxide or potassium hydroxide). The pH value may be further adjusted using acids, e.g., acetic acid, and bases, e.g., trialkylamine, but the temperature is preferably within the above range. The aprotic polar solvent (or a mixture of solvents) is then added. The acylating agent is subsequently added. The reaction is typically allowed to proceed to completion (can be monitored by HPLC) which is typically obtained within 0.24 hours, such as 0.2–1 hour, before addition of water and an acid, e.g., acetic acid, to pH 6.5–9.0. The product is typically isolated and purified by HPLC, or is precipitated by isoelectric pH, or is hydrolyzed (step (b)) before purification.

When an acylating agent of the formula I where $R^4$ is hydrogen is used, the N-acylated peptide or protein carrying lipophilic moieties and free carboxylic groups is obtained directly. Thus, the variant where $R^4$ is hydrogen represents a preferred embodiment of the method of the present invention.

Alternatively, i.e., when the group $R^4$ is $C_{1-12}$-alkyl or benzyl, the N-acylated peptide ester (or protein ester) is saponified under basic conditions so as to obtain the N-acylated peptide or N-acylated protein. Saponification is typically performed in a 0.01–4.0 M solution of an alkalimetal hydroxide, e.g., sodium or potassium hydroxide. The pH of the solution is typically 10–14. The reaction is typically allowed to proceed for 0.1–12 hours, preferably for 0.5–4 hours, at 0–40° C. such as around room temperature. After reaction, the product is purified, e.g., by precipitation at isoelectric pH and/or by preparative HPLC. Thus, the variant where $R^4$ is $C_{1-12}$-alkyl or benzyl represents another preferred embodiment of the method of the present invention.

The present invention also relates to the following aspects:

Aspect 1. A method for acylating an amino group of a peptide or a protein, the method comprising:

(a) reacting a peptide having at least one free amino group with an acylating agent of the formula I

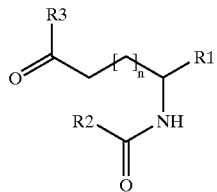

wherein
n is 0–8;
$R^1$ is $COOR^4$;
$R^2$ is a lipophilic moiety;
$R^3$ together with the carboxyl group to which $R^3$ is attached designate a reactive ester or a reactive N-hydroxy imide ester; and
$R^4$ is selected from hydrogen, $C_{1-12}$-alkyl and benzyl, under basic conditions in a mixture of an aprotic polar solvent and water; and (b) if $R^4$ is not hydrogen, saponifying the acylated peptide ester group ($COOR^4$) under basic conditions;

in order to obtain an N-acylated peptide.

Aspect 2. A method according to aspect 1, wherein $R^4$ is hydrogen.

Aspect 3. A method according to aspect 1, wherein $R^4$ selected from $C_{1-8}$-alkyl and benzyl.

Aspect 4. A method according to any of aspects 1–3, wherein the $R^3$ together with the carboxyl group to which $R^3$ is attached designate a reactive N-hydroxy imide ester.

Aspect 5. A method according to any of aspects 1–4, wherein the mixture of the aprotic solvent and water is a 1:5 to 5:1 mixture of N-methyl-2-pyrrolidone and water.

Aspect 6. A method according to any of aspects 1–5, wherein the pH of the reaction mixture in step (a) is in the range of 9–13.

Aspect 7. A method according to any of aspects 1–6, wherein the temperature of the reaction mixture in step (a) is in the range of 0–50° C.

Aspect 8. A method according to any of the aspects 3–7, wherein the acylated peptide ester is saponified at a pH value in the range of 10–14.

Aspect 9. A method according to any of the preceding aspects wherein $R^2$ is selected from $C_{3-39}$-alkyl, $C_{3-39}$-alkenyl, $C_{3-39}$-alkadienyl and steroidal residues.

Aspect 10. A compound of the formula I

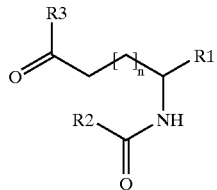

wherein
n is 0–8;
$R^1$ is COOH;
$R^2$ is a lipophilic moiety; and
$R^3$ together with the carboxyl group to which $R^3$ is attached designate a reactive ester or a reactive N-hydroxy imide ester.

Aspect 11. A compound according to aspect 10, wherein n is 0 or 1 and the $R^3$ together with the carboxyl group to which $R^3$ is attached designate a reactive N-hydroxy imide ester.

Aspect 12. A compound according to any of the aspects 10–11, wherein $R^2$ is selected from $C_{3-39}$-alkyl, $C_{3-39}$-alkenyl, $C_{3-39}$-alkadienyl and steroidal residues.

EXAMPLES

Preparation of Starting Materials

Example 1

Preparation of N-hexadecanoylglutamic acid α-benzyl ester

Glutamic acid x-benzylester (4.75 g, 20.0 mmol) was suspended in N-methyl-2-pyrrolidone (100 ml) at 20–25° C. Triethylamine (2.53 g, 25.0 mmol) and then 1-hexadecanoylbenzotriazole (7.15 g, 20.0 mmol) were added. The reaction mixture was stirred at 20–25° C. for 22 hours. To the resulting solution 0.2 M hydrochloric acid (250 ml) was added. The resulting suspension was cooled to 0° C. for 3 hours. The product was isolated by filtration, washed with water (50 ml×4), and dried to constant weight under reduced pressure and at 40° C.

Yield: 9.15 g (96%) of white material, melting at 90.0° C. (peak value) determined by Differential Scanning Calorimetry (DSC).

Example 2

Preparation of N-hexadecanoylglutamic acid α-methyl ester

Under similar reaction conditions as described in Example 1, N-hexadecanoylglutamic acid α-methyl ester was prepared, using 8.06 g (50.0 mmol) glutamic acid α-methylester.

Yield: 17.70 g (88%) of white material, melting at 95.4° C. (peak value) determined by DSC.

Example 3

Preparation of N-hexadecanoylglutamic acid α-benzyl ester γ-N-hydroxysuccinimide ester N-hexadecanoylglutamic acid α-benzyl ester (23.78 g, 50.0 mmol) was dissolved in tetrahydrofuran (200 ml) at 20–25° C. N-hydroxysuccinimide (5.75 g, 50.0 mmol), and then dicyclohexylcarbodiimide (10.32 g, 50.0 mmol) were added. The reaction mixture was stirred at 20–25° C. for 20 hours. The resulting suspension was filtered, and the filtrate evaporated to dryness under reduced pressure. The crystalline residue was dissolved in acetone (100 ml) at 40° C., and clarified by filtration. To the filtrate n-heptane (300 ml) was added. The resulting suspension was stirred for 4 hours at 20–25° C., then cooled to 0°C. for ½ hour. The product was isolated by filtration, washed with n-heptane (50 ml×3), and dried to constant weight under reduced pressure at 40° C.

Yield: 23.75 g (83%) of white material, melting at 98.6° C. (peak value) determined by DSC.

Example 4

Preparation of N-hexadecanoylglutamic acid α-methyl ester γ-N-hydroxysuccinimide ester Under similar reaction conditions as described in Example 3, N-hexadecanoylglutamic acid (α-methyl ester γ-N-hydroxysuccinimide ester was prepared, using 8.00 g (20 mmol) N-hexadecanoylglutamic acid oc-methyl ester.

Yield: 6.45 g (65%) of white material, melting at 106.0° C. (peak value) determined by DSC.

Example 5
Preparation of N-hexadecanoylglutamic acid γ-N-hydroxysuccinimide ester N-hexadecanoylglutamic acid α-benzyl ester γ-N-hydroxysuccinimide ester (5.73 g, 10.0 mmol) was dissolved in acetone (100 ml) at 20–25° C. 100% Palladium on Carbon paste (approx. 0.25 g as dry material) was added. The suspension was stirred under hydrogen until the consumption of hydrogen stopped (290 ml hydrogen, 45 minutes). The catalyst was removed by filtration, and the filtrate was evaporated to dryness under reduced pressure at 20–25° C. The residue was dissolved in acetone (25 ml) at 20–25° C., and clarified by filtration. To the filtrate n-heptane (200 ml) was added. The resulting suspension was stirred at 20–25° C. for 1 hour. The product was isolated by filtration, washed with n-heptane (50 ml×2) and dried to constant weight under reduced pressure at 40° C.

Yield: 4.20 (87%) of white material, melting at 100.8° C. (peak value) determined by DSC.

Preparation of Acylated GLP-1 Analogues

Example 6
Preparation of Arg$^{34}$Lys$^{26}$-[N-ε-(γ-Glu(N-hexadecanoyl))]-GLP-1$^{7-37}$ Arg$^{34}$-GLP-1$^{7-37}$ (5.0 g of frozen iso-precipitated peptide material, approx. 0.15 mmol) was dissolved in water (25 ml) at 0–5° C. The pH of the solution was adjusted to 12.5 by the addition of 1.0 M sodium hydroxide (2.25 ml). After 2 minutes N-methyl-2-pyrrolidone (50 ml) and 1.0 M acetic acid (1.25 ml) was added, keeping the temperature at 15° C. Triethylamine (0.2 ml) and then N-hexadecanoylglutamic acid γ-N-hydroxysuccinimide ester (97.0 mg, 0.20 mmol) were added. After 30 minutes at 15° C. water (50 ml) was added, and the pH was adjusted to 8.0 by addition of 1.0 M acetic acid (1.70 ml).

Yield: By analytical RP-HPLC the reaction mixture was shown to contain 77% (by area) of Arg$^{34}$Lys$^{26}$-[N-ε-(γ-Glu(N-hexadecanoyl))]-GLP-1$^{7-37}$.

Final purification of the product was obtained by column chromatography.

Example 7
Preparation of Arg$^{34}$Lys$^{26}$-[N-ε-(γ-Glu-OMe(N-hexadecanoyl))]-GLP-1$^{7-37}$ Under similar reaction conditions as described in Example 6, Arg$^{34}$-GLP-1$^{7-37}$ was acylated using N-hexadecanoylglutamic acid α-methyl ester γ-N-hydroxysuccinimide ester.

Yield: By analytical RP-HPLC the reaction mixture was shown to contain 64% (by area) of Arg$^{34}$Lys$^{26}$-[N-ε-(γ-Glu-OMe(N-hexadecanoyl))]-GLP-1$^{7-37}$. The product could be isolated as a precipitate by adjusting the pH of the reaction mixture to 6.0 using 1 M acetic acid. Alternatively the reaction mixture could be used directly as described in the subsequent Example 8.

Example 8
Preparation of Arg$^{34}$Lys$^{26}$-[N-ε-(γ-Glu(N-hexadecanoyl))]-GLP-1$^{7-37}$ The reaction mixture containing the product obtained in Example 7 was subjected to a basic hydrolysis by adjusting the pH to 12–13 using 1 M sodium hydroxide. The temperature of the reaction mixture was kept at 8–18° C. After 2 hours the reaction was completed, and the pH of the reaction mixture was adjusted to 7.45 by addition of 1 M acetic acid.

Yield: By analytical RP-HPLC the reaction mixture was shown to contain 65% (by area) of Arg$^{34}$Lys$^{26}$-[N-ε-(γ-Glu(N-hexadecanoyl))]-GLP-1$^{7-37}$.

Final purification of the product was obtained by column chromatography.

Example 9
The following compounds are prepared analogous to the compound of example 6, and final purification of the product is obtained by column chromatography:
Arg$^{26,34}$,Lys$^{36}$-(N-ε-(γ-Glu(N-hexadecanoyl)))-GLP-1$^{7-36}$,
Arg$^{26}$,Lys$^{34}$-(N-ε-(γ-Glu(N-hexadecanoyl)))-GLP-1$^{7-3}$, and
Gly$^8$,Arg$^{26,34}$,Glu$^{37}$,Lys$^{38}$-(N-ε-(γ-Glu(N-hexadecanoyl)))-GLP-1$^{7-38}$.

What is claimed is:

1. A method for acylating an amino group of a peptide or a protein, the method comprising:

(a) reacting a peptide or protein having at least one free amino group with an acylating agent of formula I

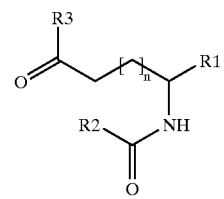

wherein
n is 0–8;
R$^1$ is COOR$^4$;
R$^2$ is a lipophilic moiety;
R$^3$ and its attached carboxyl group designate a reactive ester or a reactive N-hydroxy imide ester; and
R$^4$ is selected from the group consisting of hydrogen, C$_{1-12}$-alkyl and benzyl, under basic conditions in a mixture of an aprotic polar solvent and water; and (b) if R$^4$ is not hydrogen, saponifying the acylated peptide or protein ester group (COOR$^4$) under basic conditions;

in order to obtain an N-acylated peptide or an N-acylated protein.

2. The method of claim 1, wherein R$^4$ is hydrogen.

3. The method of claim 1, wherein R$^4$ is C$_{1-8}$-alkyl or benzyl.

4. The method of claim 1, wherein R$^3$ and its attached carboxyl group designate a reactive N-hydroxy imide ester.

5. The method of claim 1, wherein the mixture of the aprotic solvent and water is a 1:5 to 5:1 mixture of N-methyl-2-pyrrolidon and water.

6. The method of claim 1, wherein the reaction between the peptide or protein and the acylating agent in step (a) is conducted at a pH range of 9–13.

7. The method of claim 1, wherein the reaction between the peptide or protein and the acylating agent in step (a) is conducted at a temperature range of 0–5° C.

8. The method of claim 1, wherein the acylated peptide ester is saponified at a pH value in the range of 10–14.

9. The method of claim 1, wherein R$^2$ is selected from the group consisting of C$_{3-39}$-alkyl, C$_{3-39}$-alkenyl, C$_{3-39}$-alkadienyl and steroidal residues.

10. The method of claim 1, wherein R$^2$ is C$_{7-25}$-alkyl.

11. The method of claim 1, wherein the peptide is selected from the group consisting of GLP-1(7–37) and analogues thereof, exendin and analogues thereof, and GLP-2(1–34) and analogues thereof.

12. The method of claim 1, wherein the peptide is selected from the group consisting of exendin-3, exendin-4, Arg$^{26}$-GLP-1(7–37), Arg$^{34}$-GLP-1(7–37), Val$^8$GLP-1(7–37), Thr⁸GLP-1(7–37), Met⁸GLP-1(7–37), Gly⁸GLP-1(7–37), Val⁸GLP-1(7–36) amide, Thr⁸GLP-1(7–36) amide, Met⁸GLP-1(7–36) amide, and Gly⁸GLP-1(7–36) amide.

13. A compound of formula I

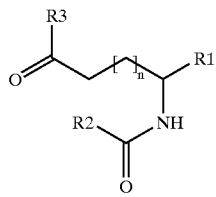

wherein
n is 0–8;
$R^1$ is $COOR^4$;
$R^2$ is a lipophilic moiety;
$R^3$ and its attached carboxyl group designate a reactive ester or a reactive N-hydroxy imide ester; and
$R^4$ is selected from the group consisting of hydrogen, $C_1$–$C_{12}$ alkyl and benzyl.

14. The compound of claim 13, wherein n is 0 or 1 and $R^3$ and its attached carboxyl group designate a reactive N-hydroxy imide ester.

15. The compound of claim 13, wherein $R^2$ is selected from the group consisting of $C_{3\text{-}39}$-alkyl, $C_{3\text{-}39}$-alkenyl, $C_{3\text{-}39}$-alkadienyl and steroidal residues.

16. The compound of claim 13, wherein $R^4$ is hydrogen.

17. The method of claim 1, wherein the mixture of the aprotic solvent and water is a 1:10 to 10:1 mixture.

* * * * *

UNITED STATES PATENT AND TRADEMARK OFFICE
CERTIFICATE OF CORRECTION

PATENT NO.     : 6,451,974 B1
DATED          : September 17, 2002
INVENTOR(S)    : Louis Brammer Hansen It is certified that error appears in the above-identified patent and that said Letters Patent is hereby corrected as shown below:

<u>Title page</u>,
Item [74], *Attorney, Agent, or Firm*, "Rezo" should read -- Reza --.

<u>Column 12</u>,
Line 48, "N-methyl-2-pyrrolidon" should read -- N-methyl-2-pyrrolidone --.
Line 54, "range of 0-5ºC" should read -- range of 0-50ºC --.

Signed and Sealed this

Twenty-seventh Day of April, 2004

JON W. DUDAS
*Acting Director of the United States Patent and Trademark Office*